(12) United States Patent
Rao et al.

(10) Patent No.: US 9,538,944 B2
(45) Date of Patent: Jan. 10, 2017

(54) NON-INVASIVE ANALYTE SENSING SYSTEM AND METHOD

(75) Inventors: Govind Rao, Ellicott City, MD (US);
Yordan Kostov, Columbia, MD (US);
Xudong Ge, Woodstock, MD (US);
Leah Tolosa, Crownsville, MD (US);
Hyung Woo, Baltimore, MD (US);
Rose Viscardi, Timonium, MD (US)

(73) Assignee: University of Maryland Baltimore County, Baltimore, MD (US)

( * ) Notice: Subject to any disclaimer, the term of this patent is extended or adjusted under 35 U.S.C. 154(b) by 538 days.

(21) Appl. No.: 13/823,903

(22) PCT Filed: Sep. 30, 2011

(86) PCT No.: PCT/US2011/054437
§ 371 (c)(1),
(2), (4) Date: Jul. 8, 2013

(87) PCT Pub. No.: WO2012/045047
PCT Pub. Date: Apr. 5, 2012

(65) Prior Publication Data
US 2013/0281806 A1    Oct. 24, 2013

Related U.S. Application Data

(60) Provisional application No. 61/388,170, filed on Sep. 30, 2010.

(51) Int. Cl.
*A61B 5/1455*    (2006.01)
*A61B 5/00*    (2006.01)

(52) U.S. Cl.
CPC ......... *A61B 5/14552* (2013.01); *A61B 5/6807* (2013.01); *A61B 5/6829* (2013.01)

(58) Field of Classification Search
None
See application file for complete search history.

(56) References Cited

U.S. PATENT DOCUMENTS

| 5,034,189 A * | 7/1991 | Cox ..................... G01N 21/643 422/423 |
| 2004/0029170 A1 | 2/2004 | Wolfram et al. |
| 2006/0020179 A1* | 1/2006 | Anderson ................ A61B 5/01 600/309 |
| 2006/0063993 A1* | 3/2006 | Yu ...................... A61B 5/14532 600/322 |

(Continued)

OTHER PUBLICATIONS

Finer N, Leone T. Oxygen saturation monitoring for the preterm infant: the evidence basis for current practice. Pediatr Res 2009; 65 (4):375-80.

(Continued)

*Primary Examiner* — Eric Winakur
*Assistant Examiner* — Marjan Fardanesh
(74) *Attorney, Agent, or Firm* — Rene A. Vazquez, Esq.

(57) ABSTRACT

A non-invasive gas analyte sensing and monitoring system and method is provided that is particularly applicable to transcutaneous monitoring of arterial blood gases in a mammal. The system and method relies on diffusion of the analyte to be measured into a diffusion chamber and remote sensing of the analyte in the diffusion chamber using optical chemical sensors and associated optoelectronics.

36 Claims, 5 Drawing Sheets

(56) References Cited

U.S. PATENT DOCUMENTS

| | | | |
|---|---|---|---|
| 2006/0166350 A1* | 7/2006 | Lowe | G01N 21/05 435/287.1 |
| 2006/0205071 A1 | 9/2006 | Hasson et al. | |
| 2008/0241966 A1* | 10/2008 | Kunnecke | A61B 5/1486 436/536 |
| 2009/0143761 A1* | 6/2009 | Cantor | A61N 1/044 604/501 |
| 2009/0156914 A1* | 6/2009 | O'Neil | A61B 5/097 600/314 |

OTHER PUBLICATIONS

Saugstad OD. Is oxygen more toxic than currently believed? Pediatrics 2001; 108 (5):1203-5.

Cunningham S, Fleck BW, Elton RA et al. Transcutaneous oxygen levels in retinopathy of prematurity. Lancet 1995; 346 (8988):1464-5.

Carlo WA, Finer NN, Walsh MC et al. Target ranges of oxygen saturation in extremely preterm infants. N Engl J Med 2010; 362 (21):1959-69.

Chen ML, Guo L, Smith LE et al. High or low oxygen saturation and severe retinopathy of prematurity: a meta-analysis. Pediatrics 2010; 125 (6):1483-92.

Flynn JT, Bancalari E, Snyder ES et al. A cohort study of transcutaneous oxygen tension and the incidence and severity of retinopathy of prematurity. N Engl J Med 1992; 326 (16):1050-4.

Jobe AH. The new BPD: an arrest of lung development. Pediatr Res 1999; 46:641-3.

Jobe AH, Bancalari E. Bronchopulmonary dysplasia. Am J Respir Crit Care Med 2001; 163:1723-9.

Erickson SJ, Grauaug A, Gurrin L et al. Hypocarbia in the ventilated preterm infant and its effect on intraventricular haemorrhage and bronchopulmonary dysplasia. J Paediatr Child Health 2002; 38 (6):560-2.

Gannon CM, Wiswell TE, Spitzer AR. Volutrauma, PaCO2 levels, and neurodevelopmental sequelae following assisted ventilation. Clin Perinatol 1998; 25 (1):159-75.

Murase M, Ishida A. Early hypocarbia of preterm infants: its relationship to periventricular leukomalacia and cerebral palsy, and its perinatal risk factors. Acta Paediatr 2005; 94 (1):85-91.

Takahashi R, Yamada M, Takahashi T et al. Risk factors for cerebral palsy in preterm infants. Early Hum Dev 2005; 81 (6):545-53.

Garland JS, Buck RK, Allred EN et al. Hypocarbia before surfactant therapy appears to increase bronchopulmonary dysplasia risk in infants with respiratory distress syndrome. Arch Pediatr Adolesc Med 1995; 149 (6):617-22.

Hagen EW, Sadek-Badawi M, Carlton DP et al. Permissive hypercapnia and risk for brain injury and developmental impairment. Pediatrics 2008; 122 (3):583-9.

Kaiser JR, Gauss CH, Pont MM et al. Hypercapnia during the first 3 days of life is associated with severe intraventricular hemorrhage in very low birth weight infants. J Perinatol 2006; 26 (5):279-85.

Thome UH, Ambalavanan N. Permissive hypercapnia to decrease lung injury in ventilated preterm neonates. Semin Fetal Neonatal Med 2009; 14 (1):21-7.

Hauspurg AK, Allred EN, Vanderveen DK et al. Blood Gases and Retinopathy of Prematurity: The ELGAN Study. Neonatology 2010; 99 (2):104-11.

Severinghaus JW. The current status of transcutaneous blood gas analysis and monitoring. Blood Gas News 1998; 7 (2):4-9.

Quine D, Stenson BJ. Does the monitoring method influence stability of oxygenation in preterm infants? A randomised crossover study of saturation versus transcutaneous monitoring. Arch Dis Child Fetal Neonatal Ed 2008; 93 (5):F347-50.

Tobias JD. Transcutaneous carbon dioxide monitoring in infants and children. Pediatr Anesth 2009; 19 (5):434-44.

Bemet-Buettiker V, Ugarte MJ, Frey B et al. Evaluation of a new combined transcutaneous measurement of PCO2/pulse oximetry oxygen saturation ear sensor in newborn patients. Pediatrics 2005; 115 (1):e64-8.

Lacerenza S, De Carolis MP, Fusco FP et al. An evaluation of a new combined Spo2/PtcCO2 sensor in very low birth weight infants. Anesth Analg 2008; 107 (1):125-9.

Raju, TK, Stevenson, DK, Higgins, RD, Stark AR. Safe and Effective Devices for use in the Neonatal Intensive Care Units: NICHD Workshop Summary. Biomed Instr Technol 2009 43:408-418.

Szmacinski H, J. R. Lakowicz,. Lifetime-Based Sensing. In: Jr Lakowicz, editor, translator and editor Topics in Fluorescence Spectroscopy. New York: Plenum Press; 1994; p. 295.

Bambot SB, Holavanahali R, Lakowicz JR et al. Phase fluorometric sterilizable optical oxygen sensor. Biotechnol Bioeng 1994; 43 (11):1139-45.

Nagl S, Baleizao C, Borisov SM, Schaferling M. Optical Sensing and Imaging of Trace Oxygen with Record Response. Angew. Chem. Int. Ed. 2007, 46, 2317-2319.

Ge XD, Kostov Y, Rao G. High-stability non-invasive autoclavable naked optical CO2 sensor. Biosensors & Bioelectronics 2003; 18 (7):857-65.

Ge XD, Kostov Y, Rao G. Low-cost noninvasive optical CO2 sensing system for fermentation and cell culture. Biotechnology and Bioengineering 2005; 89 (3):329-34.

Tolosa L, Kostov Y, Harms P et al. Noninvasive measurement of dissolved oxygen in shake flasks. Biotechnol Bioeng 2002; 80 (5):594-7.

\* cited by examiner

RESPONSES FOR STEP CHANGES FROM 228 → 0 μtorr
AND 0 → 228 μtorr $CO_2$

FIG. 5

TYPICAL SHAPE OF $P$ VS $t$ PLOT AND CHANGES IN P IN THE FIRST 2 MINUTES.

FIG. 6

NON-INVASIVE ANALYTE SENSING SYSTEM AND METHOD

This application claims priority to U.S. Provisional Application Ser. No. 61/388,170, filed Sep. 30, 2010, whose entire disclosure is incorporated herein by reference.

BACKGROUND OF THE INVENTION

1. Field of the Invention

The present invention relates to non-invasive sensing of substances such as, for example, non-invasive sensing of transcutaneous blood gases for respiratory management in patients.

2. Background of the Related Art

The Background of the Related Art and the Detailed Description of Preferred Embodiments below cite numerous technical references, which are listed in the Appendix below. The numbers shown in parenthesis at the end of some of the sentences refer to specific references listed in the Appendix. For example, a "(1)" shown at the end of a sentence refers to reference "1" in the Appendix below. All of the references listed in the Appendix below are incorporated by reference herein in their entirety.

Challenges of Preterm Birth

Optimal cellular functioning depends on an adequate supply of oxygen and acid-base balance. Highly complex biologic systems have evolved to maintain cellular functions during aberrant conditions of low and high oxygen exposures and to correct acid-base imbalance. When these systems are overwhelmed, cellular damage occurs. The fetus, which is dependent on the placenta for gas exchange, is exposed to relatively low oxygen concentrations and antioxidant defense mechanisms are under-developed (1).

Preterm birth requires technologies for supporting immature organ systems on the one hand, while minimizing technology-induced injury on the other that may contribute to long-term adverse outcomes. Specific problems of this kind are extremes in arterial partial pressure of oxygen ($PaO_2$) and carbon dioxide ($PaCO_2$). A variety of pathological conditions are known to result from both hypoxemia and hyperoxia. However, current understanding is that the range for acceptable $PaO_2$ is quite narrow. Similarly, hypocarbia or hypercarbia can result in brain or ocular pathology. The optimal range of $PaCO_2$ has not been established, but avoiding extremes is critical for survival.

Consequences of Hypoxia and Hyperoxia

Severe hypoxemia that can occur in utero as a result of acute or chronic placental dysfunction, or postnatally in infants with cyanotic congenital heart disease or neonatal lung disease, may cause brain injury, multi-organ failure, pulmonary hypertension, and death. Although oxygen therapy for newborns has been used in the United States since the 1930s, its relationship to retinopathy of prematurity (ROP) (previously retrolental fibroplasia), a potentially blinding disease, was not recognized until the 1950s (2). Fluctuations in arterial partial pressure of oxygen ($PaO_2$)(i.e. swings from hypoxia to hyperoxia) also increase the risk for ROP, underscoring the need for monitoring devices that are responsive to rapid changes in $PaO_2$ (3). Efforts to define an optimal oxygen target range to minimize the incidence of ROP continue to the present (4, 5, 6).

Pulmonary oxygen toxicity contributes to bronchopulmonary dysplasia (BPD), the major respiratory morbidity of prematurity characterized by an arrest of alveolar development (7, 8). As summarized by Finer and Leone, "the therapeutic index for oxygen use seems to be much narrower than previously realized, and we have yet to define the optimal oxygen exposure for the most premature infants" (1).

Consequences of Hypocarbia and Hypercarbia

Extremes in arterial partial pressure of carbon dioxide ($PaCO_2$) also contribute to neonatal morbidities. Hypocarbia in the first few days of life may contribute to altered cerebral blood flow in the preterm infant. Potential consequences include intraventricular hemorrhage (IVH), periventricular leukomalacia (white matter injury), and cerebral palsy (9, 10, 11, 12). Hypocarbia resulting from overventilation contributes to volutrauma and the development of BPD (13). Permissive hypercapnea has been proposed as a strategy to limit lung injury, but the safety of this practice has not been established (14, 15, 16). Indeed, early exposure to hypercarbia and associated acidosis increases the risk for severe ROP and IVH (17, 15).

The optimal range of $PaCO_2$ has not been established in the neonatal population, but clearly, rapid recognition of and response to extremes in $PaCO_2$ is critical for survival and minimizing morbidities.

Status of Neonatal Blood Gas Monitoring

For the reasons discussed above, arterial blood gas (ABG) measurements are indispensable for respiratory management in the neonatal intensive care unit (NICU). Although arterial blood gas (ABG) measurements remain the gold standard for guiding respiratory management in the NICU, the necessity for placement of indwelling arterial lines or intermittent arterial or heel blood sampling are associated with potential complications such as infection, thrombus formation, bleeding, and procedure-associated pain. In addition, the frequency of blood sampling often necessitates blood transfusions to replace blood volume. Further, ABGs, at best provide only intermittent information concerning dynamic changes in blood gases.

To address these concerns, non-invasive devices have been developed to continuously monitor blood gases. In the 1970s, transcutaneous monitors were developed to measure the amount of $O_2$ ($tcPO_2$) and $CO_2$ ($tcCO_2$) dissolved in tissue that approximated arterial values when the skin underneath the sensor was heated to 43-44° C. (18). Disadvantages included the potential for skin burns, necessitating frequent sensor site changes and re-calibration. Accuracy was affected by skin thickness, peripheral perfusion, and use of vasopressors (18).

Since its introduction in the 1980s, pulse oximetry, which measures the proportion of hemoglobin in arterial blood that is bound to oxygen, has largely replaced $tcPO_2$ monitors in most NICUs. Pulse oximeters are easy to use, and do not require heating the skin or calibration. However, false alarms may occur due to motion artifacts. In addition, due to the shape of the hemoglobin-oxygen dissociation curve, small changes in oxygen saturation ($SpO_2$)>95% can fail to detect large increases in $PaO_2$, thus limiting the usefulness of pulse oximetry for detection of hyperoxia (19). In addition, compared to $SpO_2$ monitoring, $tcPO_2$ monitoring was associated with less variability in oxygen tension and greater proportion of time spent within the oxygen target range (19).

$TcPCO_2$ monitoring is more accurate than end-tidal $CO_2$ monitors in patients with shunt or ventilation/perfusion inequalities, and can be used in situations such as high frequency or non-invasive ventilation where $ET-CO_2$ cannot (20). Recently, a $SpO_2/tcPCO_2$ combination sensor and a neonatal sized $tcO_2/tcPCO_2$ combination sensor based on current technology have been introduced (21, 22).

To address some of the above concerns, transcutaneous monitors for $O_2$ ($tcpO_2$) and $CO_2$ ($tcCO_2$) using electrochemical sensors have been used. However, these electrodes have at least the following disadvantages: (1) they suffer from calibration drift due to depletion of the electrolyte; (2) they lack sensitivity at low $O_2$ due to consumption of $O_2$ by the Clark electrode; (3) the potential for membrane failure; (4) the use of adhesives to maintain direct skin contact; and (5) the possibility of burns from raising skin temperature to 43° C. for $tcpO_2$ monitoring. The last two issues, in particular, can lead to serious skin injury. Given the drawbacks of current technologies, it is clear that a new generation of neonatal monitoring devices is needed that is: (1) non-invasive/painless; (2) more accurate and sensitive than current sensors; (3) easy to use by staff; and (4) and can follow dynamic changes in blood gases for longer periods of time.

SUMMARY OF THE INVENTION

An object of the invention is to solve at least the above problems and/or disadvantages and to provide at least the advantages described hereinafter.

Therefore, an object of the present invention is to provide a system and method for the sensing of gas analytes in a non-invasive and/or non-contact manner.

Another object of the present invention is to provide a system and method for the sensing of blood gases, such as $O_2$ and $CO_2$, in a non-invasive and/or non-contact manner.

Another object of the present invention is to provide a system and method for the sensing of transcutaneous blood gases, such as $tcpO_2$ and $tcCO_2$, in a non-invasive and/or non-contact manner.

Another object of the present invention is to provide a system and method for the sensing of transcutaneous blood gases, such as $tcpO_2$ and $tcCO_2$, in a mammal in a non-invasive and/or non-contact manner.

Another object of the present invention is to provide a system and method for the sensing of transcutaneous blood gases, such as $tcpO_2$ and $tcCO_2$, in a human in a non-invasive and/or non-contact manner.

Another object of the present invention is to provide a system and method for the sensing of transcutaneous blood gases, such as $tcpO_2$ and $tcCO_2$, in an infant in a non-invasive and/or non-contact manner.

Another object of the present invention is to provide a system and method for the sensing of transcutaneous blood gases, such as $tcpO_2$ and $tcCO_2$, in a preterm infant in a non-invasive and/or non-contact manner.

To achieve at least the above objects, in whole or in part, there is provided an analyte sensing system, comprising a diffusion chamber adapted to receive at least a portion of an object containing at least one analyte to be measured, a measurement chamber pneumatically coupled to the diffusion chamber thereby adapted to receive at least a portion of one or more analytes from the diffusion chamber when the one or more analytes are present in the diffusion chamber, at least one sensor positioned in the measurement chamber that is adapted to chemically interact and/or to physically react with a respective analyte, and at least one optoelectronic component positioned outside the measurement chamber for remotely detecting the chemical interaction and/or the physical reaction of the at least one sensor.

To achieve at least the above objects, in whole or in part, there is also provided a non-invasive transcutaneous blood gas sensing system for determining information on arterial blood gas in a mammal, comprising a diffusion chamber adapted to receive a mammalian appendage, a measurement chamber pneumatically coupled to the diffusion chamber, thereby adapted to receive at least a portion of one or more analytes from the diffusion chamber when the one or more analytes diffuse transcutaneously from the mammalian appendage into the diffusion chamber, at least one optical chemical sensor positioned in the measurement chamber that is adapted to chemically interact and/or physically react with a respective analyte, and at least one optoelectronic component positioned outside the measurement chamber for remotely detecting the chemical interaction and/or the physical interaction of the at least one optical chemical sensor.

To achieve at least the above objects, in whole or in part, there is also provided a non-invasive transcutaneous blood gas sensing system for determining information on arterial blood gas in a mammal, comprising a combined diffusion and measurement chamber comprising at least one gas permeable surface adapted to allow transcutaneous diffusion of analytes from a mammal when the gas permeable surface is in contact with the mammal, at least one optical chemical sensor positioned in the combined diffusion and measurement chamber that is adapted to chemically interact and/or physically react with a respective analyte, and an optoelectronic system positioned outside the combined diffusion and measurement chamber for remotely detecting the chemical interaction and/or the physical interaction of the at least one optical chemical sensor.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

By way of example, the present invention will be predominantly described in connection with a non-invasive transcutaneous blood gas sensing system and method that is particularly suited for the non-invasive sensing of transcutaneous blood gas in infants. However, it should be appreciated that the present invention can be used for the noninvasive sensing and monitoring of transcutaneous blood gas in adults as well. In addition, although the present invention is described in connection with transcutaneous blood gas sensing, it can be applied to the sensing of any analyte that can diffuse through any type of permeable boundary.

Figure 1A:
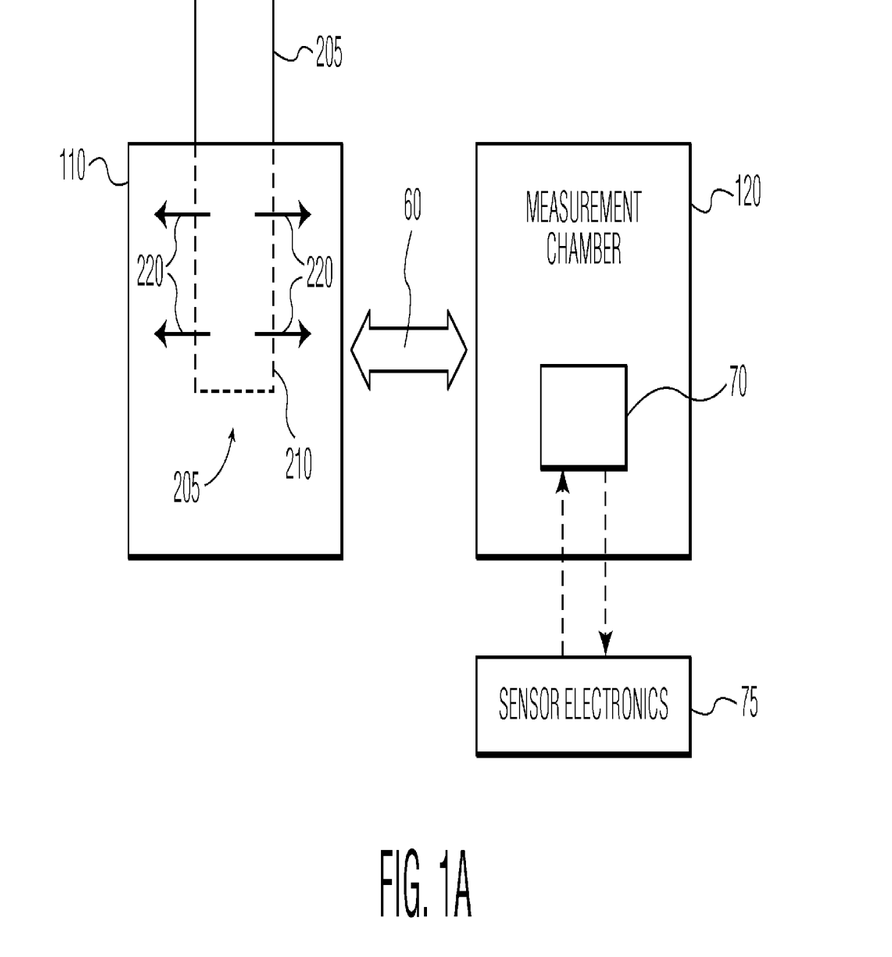
FIG. 1A is a block diagram that illustrates the principle of operation of one preferred embodiment of the present invention.

FIG. 1A is a block diagram that illustrates the principle of operation of one preferred embodiment of the present invention. The system 50 includes a diffusion chamber 110 and a measurement chamber 120 that are pneumatically coupled via pneumatic coupling components 60. The pneumatic coupling components 60 can include any combination of pneumatic components such as, for example, valves, conduits, pumps, intake ports, exhaust ports, etc.

The measurement chamber 120 includes at least one analyte sensor 70. The at least one analyte sensor 70 is preferably an optical chemical sensor that exhibits at least one property (e.g., light emission intensity, light absorption, etc.) that is dependent on the amount of the analyte that is being sensed and/or monitored. The system also includes sensor electronics 75 for receiving signals from the analyte sensor. If the analyte sensor 70 is an optical chemical sensor, then the sensor electronics also generate and direct an optical excitation signal to the analyte sensor 70.

As discussed above, the analyte sensor 70 is preferably an optical chemical sensor. However, the analyte sensor 70 can be any type of sensor known in the art for detecting the analyte being measured.

In operation, at least a portion of an object 205 in which the analyte being measured is contained is placed inside the diffusion chamber 110. The object 205 preferably has gas permeable walls 210 through which a gas analyte 220 can diffuse through. The gas analyte 220 that diffuses into the diffusion chamber is directed to the measurement chamber 120 via pneumatic coupling components 60. The gas analyte 220 is then measured the at least one optical chemical sensor 70 and the optoelectronic system 75.

The object 205 that contains the analyte being measured can be any type of object including, but not limited to, a mammalian appendage, a plant, a man-made container or vessel. Generally, the object can be any object containing an analyte that one desires to measure and that has at least one surface that is at least partially permeable to the analyte one desires to measure.

Figure 1B:
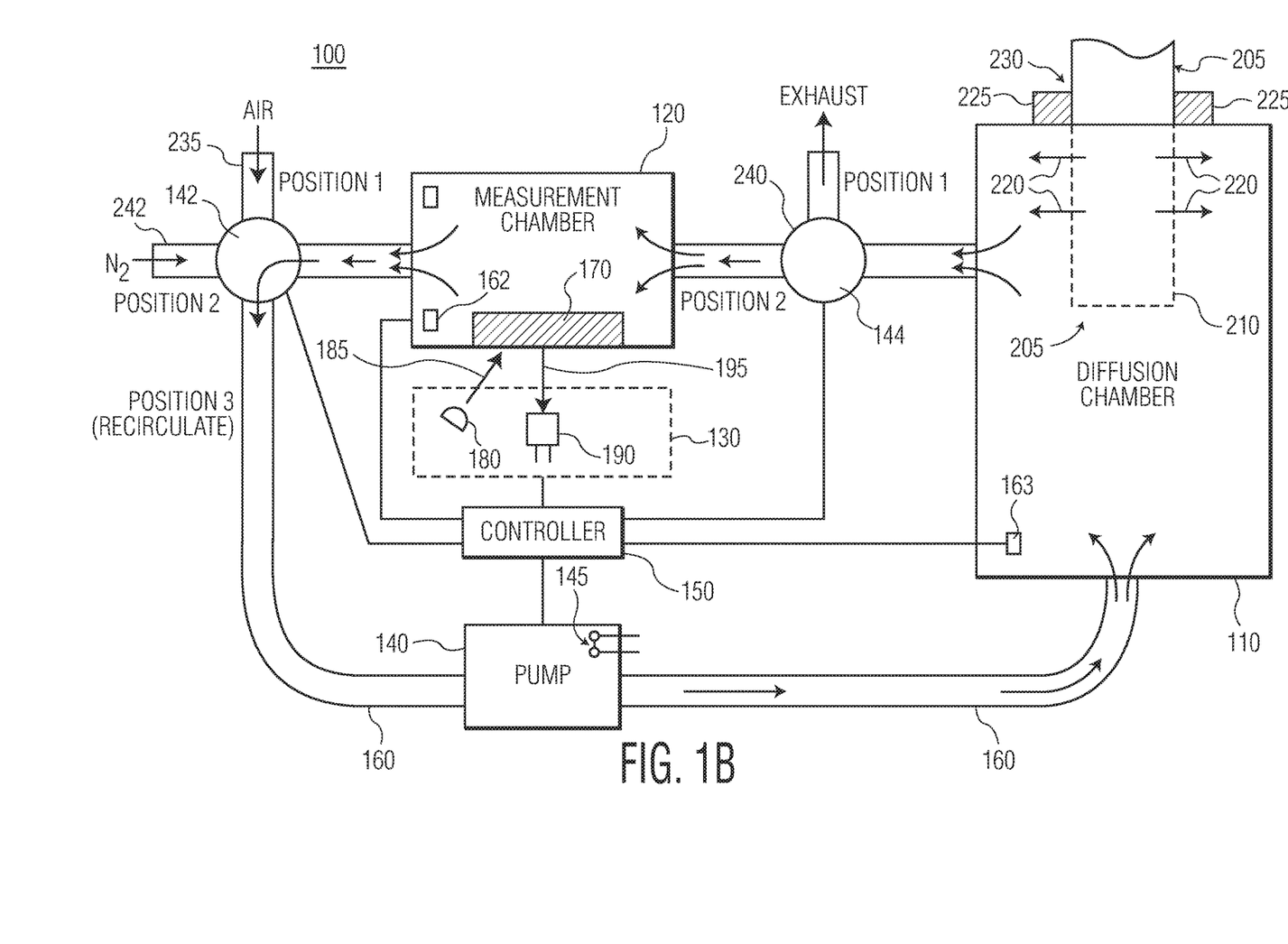
FIG. 1B is a schematic diagram of a non-invasive analyte sensing system, in accordance with a second preferred embodiment of the present invention.

FIG. 1B is a schematic diagram of a non-invasive gas analyte sensing system, in accordance with a second preferred embodiment of the present invention. The system 100 includes a diffusion chamber 110, a measurement chamber 120, optoelectronic components 130, pneumatic pump 140, three-way valve 142, two-way valve 144 and a controller 150. The measurement chamber 120 and diffusion chamber 110 are both preferably formed of a gas impermeable material such as, for example, mylar. The diffusion chamber 110, measurement chamber 120, air pump 140, and valves 142/144 are coupled together with conduits 160, thereby forming a circulation loop through which air can circulate. The air pump 140 may include a heater 145 for heating the air that is circulated, if needed. In addition, the measurement chamber 120 and the diffusion chamber 110 may optionally include respective heaters 162 and 163 that can be independently controlled by the controller 150 for independent control of temperature in each chamber. The conduits 160 can be any conduit capable of circulating air/gas such as, for example, Tygon® tubing.

The measurement chamber includes at least one optical chemical sensor 170 which, when excited with excitation light, generates light emission. The light emitted by the optical chemical sensor exhibits at least one property (e.g., intensity, absorption) that is dependent on the amount of the analyte that is being sensed and/or monitored. Optoelectronic components 130 include an optical excitation source 180 for generating excitation light 185 that is used to optically excite the optical chemical sensor 170. Optoelectronic components 130 also include an optical detector 190 for detecting the light emission 195 generated by the optical chemical sensor 170. Examples of optical excitation sources include, but are not limited to, light emitting diodes (LEDs) and laser diodes. An example of an optical detector includes, but is not limited to, a photodetector.

The optical chemical sensor 170 can suitably be a sensing "cocktail", such as PDMS rubber that contains a gas-sensing dye. However, any type of sensing material known in the art can be used for the optical chemical sensor 170, as long as it emits light with at least one property (e.g., intensity, intensity decay rate) that is dependent on the amount of the analyte that is being sensed and/or monitored. By way of example, the optical chemical sensor 170 can be an oxygen sensor or a $CO_2$ sensor. The optical chemical sensor 170 may be secured to the measurement chamber 120 using any suitable means including, but not limited to, adhesives, mechanical means, magnetic means or interdigitated means (e.g., Velcro™). Specific examples of optical chemical sensors will be described below in connection with other preferred embodiments of the invention.

The optical excitation source 180 is matched to the optical chemical sensor 170 being used. That is, the output wavelength of the optical excitation source 180 should corresponds to the excitation wavelength of the optical chemical sensor 170. Although only one optical chemical sensor 170 is shown, any number of optical chemical sensors 170 can be placed inside the measurement chamber 120 in order to sense and/or monitor more than one type of analyte. Further, any number and combination of optical excitation sources 180, optical chemical sensors 170 and optical detectors 190 may be used.

In operation, at least a portion of an object 205 in which the analyte being measured is contained is placed inside the diffusion chamber 110. The vessel 205 preferably has gas permeable walls 210 through which a gas analyte 220 can diffuse through. An airtight seal 225 is preferably used at the opening 230 through which the portion of the vessel 205 is inserted into the diffusion chamber 110 using any sealing means known in the art.

Under initial conditions, the controller 150 will operate air pump 140 and will place three-way valve 142 into position 1 and two-way valve 144 into position 1. This will close off inlet 242 and open inlet 235 in three-way valve 142, and will open the exhaust outlet 240 in two-way valve 144. The result is that ambient air will be drawn into conduit 160 via inlet 235. The ambient air will then flow through the diffusion chamber 110 and out of exhaust port 240.

The controller 150 controls the measurement process, including control of the pump 140, valves 142/144 and optoelectronic components 130. When a measurement is ready to be made, the controller 150 will initiate a flush sequence, which will place three-way valve 142 into position 2 and two-way valve into position 1. This will close off inlet 235 and open inlet 242 in three-way valve 142, and will open the exhaust port 240 in two-way valve 144. This will flush the diffusion chamber with nitrogen by drawing nitrogen into conduit 160 via inlet 242, passing the nitrogen through the diffusion chamber 110 and out of exhaust port 240. This flush sequence is preferably performed until the optoelectronic components 130 that are measuring the signals from the optical chemical sensor 170 output a zero reading (after accounting for instrument offsets). This ensures constant initial conditions for all measurements.

Once the flush sequence is complete, a measurement sequence is initiated. For the measurement sequence, the controller 150 places three-way valve 142 in position 3 and two-way valve 144 in position 2. This closes off inlets 235 and 242 in three-way valve 142, and closes off exhaust port 240 in two-way valve 144. This will circulate nitrogen in a continuous loop through the diffusion chamber 110 and the measurement chamber 120. The optical chemical sensor 170 is then read with optoelectronic components 130 to obtain an analyte reading.

Figure 2:
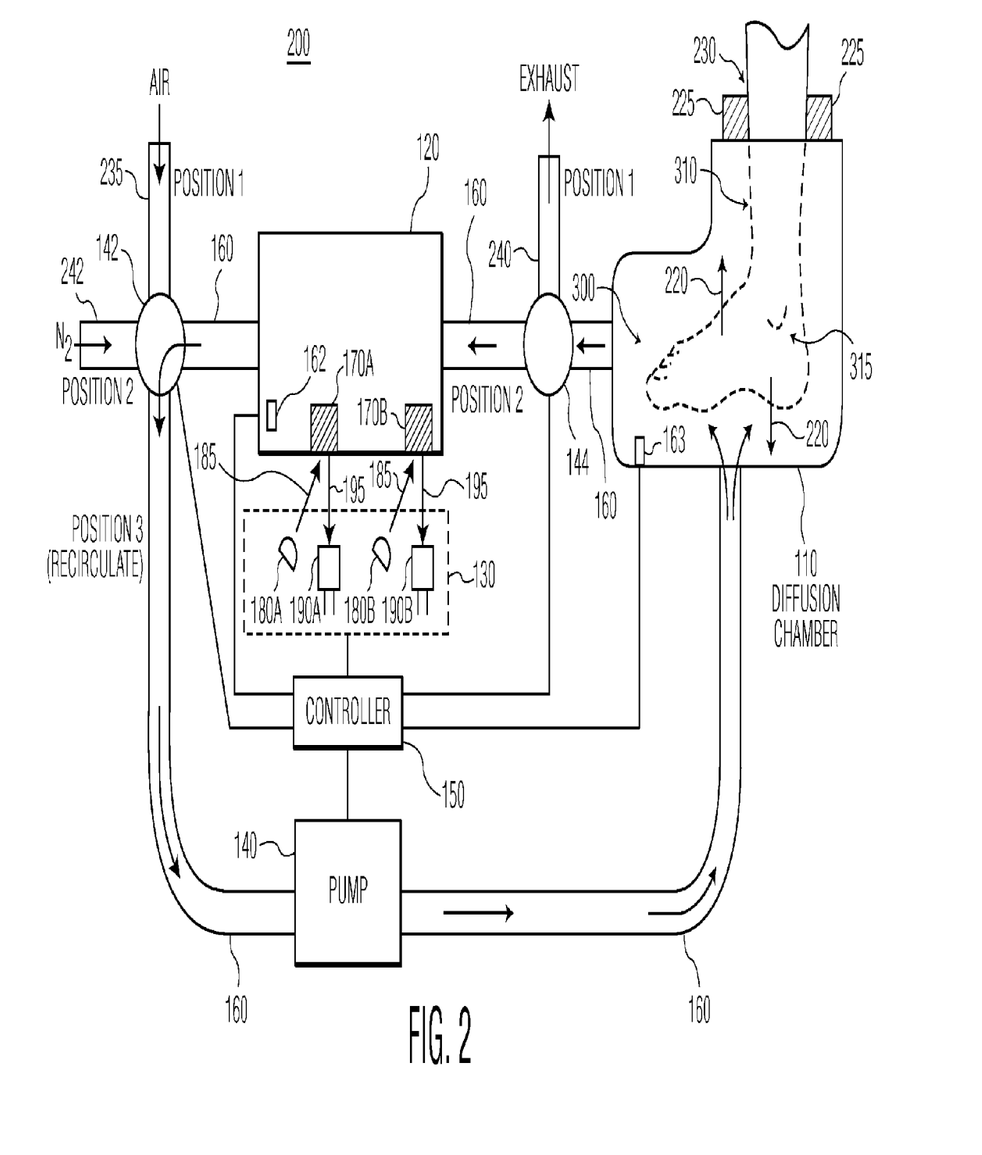
FIG. 2 is a schematic diagram of a non-invasive transcutaneous blood gas sensor 200 in accordance with a third preferred embodiment of the present invention.

FIG. 2 is a schematic diagram of a non-invasive transcutaneous blood gas sensor 200 in accordance with a third preferred embodiment of the present invention. The embodiment of FIG. 2 is similar to the embodiment of FIG. 1, and like reference numerals refer to like elements.

In the embodiment of FIG. 2, the diffusion chamber 110 is preferably "sock" shaped so as to fit over the foot 300 and ankle 315 and/or lower calf 310 of a patient. In addition, the measurement chamber 120 includes a transcutaneous $pO_2$ optical chemical sensor ("$tcpO_2$ sensor") 170A and a transcutaneous $pCO_2$ optical chemical sensor ("$tcpCO_2$ sensor") 170B. The optoelectronic components 130 include an optical excitation source 180A and optical detector 190A for optical chemical sensor 170A, and an optical excitation source 180B and optical detector 190B for optical chemical sensor 170B. Although the diffusion chamber 110 is sock-shaped, it should be appreciated that the diffusion chamber 110 can be any made in any shape while still falling within the scope of the present invention. In addition, the opening 230 of the sock-shaped diffusion chamber 110 can be designed to snugly and comfortably fit over the patient's calf 310 and/or ankle 315, thereby obviating the need for separate sealing means 225.

The principal of operation of the FIG. 2 embodiment is similar to the principal of operation of the FIG. 1 embodiment. When a measurement is ready to be made, the controller 150 will initiate a flush sequence, which will place three-way valve 142 into position 2 and two-way valve into position 1. This will close off inlet 235 and open inlet 242 in three-way valve 142, and will open the exhaust port 240 in two-way valve 144. This will flush the diffusion chamber with nitrogen by drawing nitrogen into conduit 160 via inlet 242, passing the nitrogen through the diffusion chamber 110 and out of exhaust port 240. This flush sequence is preferably performed until the optoelectronic components 130 that are measuring the signals from $tcpO_2$ sensor 170A and a $tcpCO_2$ sensor 170B output a zero reading (after accounting for instrument offsets). This ensures constant initial conditions for all measurements. Preferably, only a slight overpressure is used to avoid compression of the foot 300 and/or calf 310 and thereby avoid disruptions of the blood flow.

Once the flush sequence is complete, a measurement sequence is initiated. For the measurement sequence, the controller 150 places three-way valve 142 in position 3 and two-way valve 144 in position 2. This closes off inlets 235 and 242 in three-way valve 142, and closes off exhaust port 240 in two-way valve 144. This will circulate nitrogen in a continuous loop through the diffusion chamber 110 and the measurement chamber 120. $tcpO_2$ sensor 170A and a $tcpCO_2$ sensor 170B are then read with optoelectronic components 130 to obtain a $tcpO_2$ and $tcpCO_2$ reading.

Figure 3:
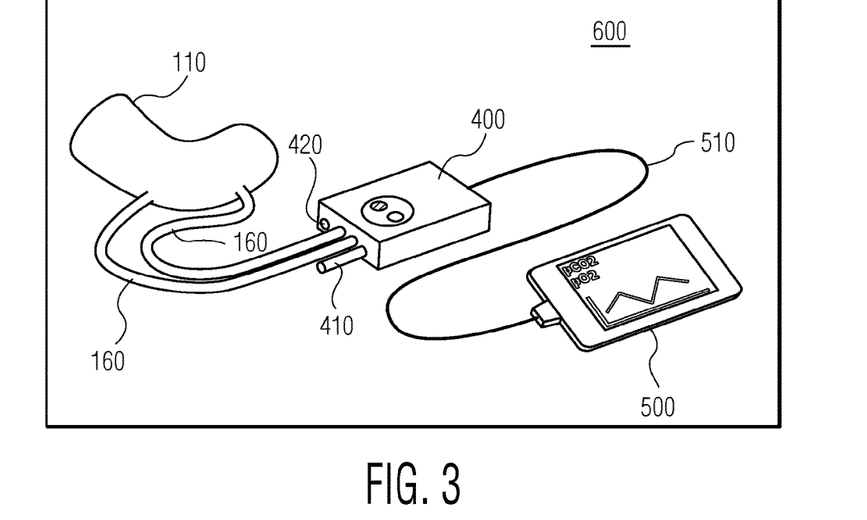
FIG. 3 is a schematic diagram of a non-invasive transcutaneous blood gas sensor 600 in accordance with a fourth preferred embodiment of the present invention.

FIG. 3 is a schematic diagram of a non-invasive transcutaneous blood gas sensor 600 in accordance with a fourth preferred embodiment of the present invention. The embodiment of FIG. 3 is similar to the embodiments of FIGS. 1 and 2, and like reference numerals refer to like elements.

The principle of operation of the FIG. 3 embodiment is similar to the embodiments of FIGS. 1 and 2. However, a sensor and pneumatic control unit 400 houses the measurement chamber 120 and the air pump 140, and performs the functionality of valves 142 and 144 of the embodiments of FIGS. 1 and 2. Nitrogen or ambient air is drawn into the circulating loop via inlet 410 and air/gas is expelled from the circulating loop via exhaust port 420. The display, data processing and storage unit 500 performs the function of the controller 150 of the FIGS. 1 and 2 embodiments, and also provides a display and storage for storing measurement data. Although the display, data processing and storage unit 500 is shown connected to the sensor and pneumatic control unit 400 via a cable 510, it can be connected wirelessly to the sensor and pneumatic control unit 400 using WiFi, Bluetooth or any other wireless connections means known in the art.

Figure 4:
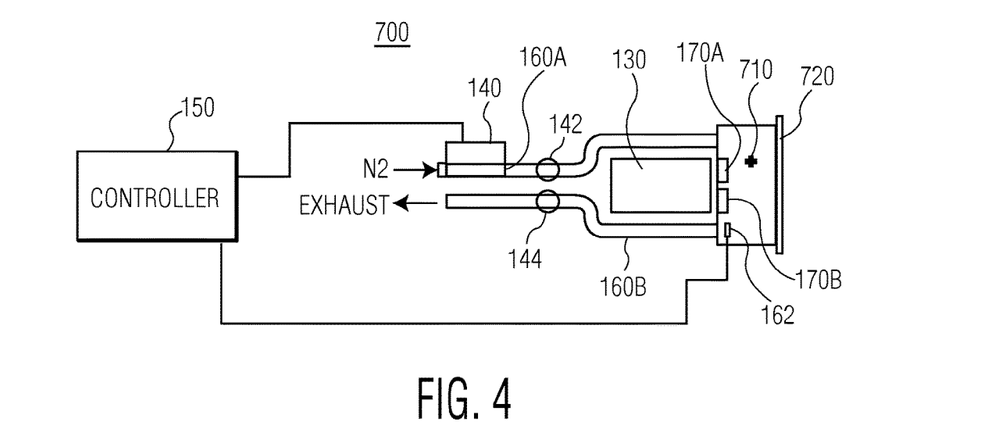
FIG. 4 is a schematic diagram of a non-invasive analyte sensing system 700, in accordance with a fifth preferred embodiment of the present invention.
Figure 5:
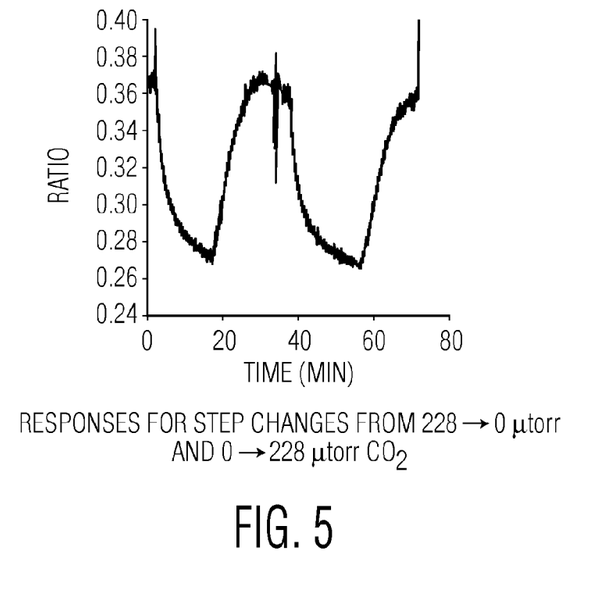
FIG. 5 is a plot of the ratio of the two excitation peaks for the protonated and deprotonated forms of HPTS in an optical $CO_2$ sensor.

FIG. 4 is a schematic diagram of a non-invasive analyte sensing system 700, in accordance with a fifth preferred embodiment of the present invention. The system 700 combines the functionality of the diffusion chamber 110 and the measurement chamber 120 into a combined chamber 710. The combined chamber 710 includes a diffusion surface 720 that is designed to contact a patient's skin or the permeable surface of a container containing the analyte to be measured. The diffusion surface 720 is at least partially permeable to the analyte being measured.

If used as a blood gas monitor, the diffusion surface 720 would be placed against any flat area of the patient's body, such as the abdomen, thigh or bottom of a foot. In operation, at the beginning of each measurement, the combined chamber 710 is flushed with nitrogen that is delivered to the combined chamber 710 via pump 140 and conduit 160A and exits the combined chamber 710 via conduit 160B. Then, valves 142 and 142 are closed so as to seal the combined chamber 710 and the measurement can begin. The optoelectronic components 130 and controller 150 operate in a manner similar to that described above in connection with the embodiments of FIGS. 1-3.

The $tcpO_2$ Sensor (170A)

Measurement of $pO_2$ sensors is based on the dynamic quenching of a fluorescent metal-ligand complex tris(diphenylphenanthroline)ruthenium (H) dichloride (25, 29). The process is described by the Stern-Volmer equation, $F_0/F=\tau_0/\tau=1+K_{SV}\times[O_2]$, where $\tau_0$ and $F_0$ are the decay time and intensity in the absence of oxygen, respectively, $\tau$ and F are the decay time and intensity in the presence of oxygen, $K_{SV}$ is the Stern-Volmer constant and [$O_2$] is the oxygen concentration. Oxygen concentrations can be correlated to either fluorescence intensity or the decay rate of the fluorophore. Of these, the decay or lifetime measurements are the preferred technique as intensity measurements tend to be unreliable due to potential photodecomposition, instability of the optical excitation source 180A or optical detector 190A, scattering or even minor optical changes in the optical path (24).

Changes in decay time in response to oxygen are performed using frequency-domain fluorometry. In this method, lifetime is measured by illuminating the sensor with intensity-modulated light from the optical excitation source 180A at a frequency ω and measuring the phase shift φ of the resulting emission. Compared with the Clark electrode, the $pO_2$ sensor is significantly more sensitive at low $pO_2$. In addition, unlike the Clark electrode, the $pO_2$ sensor does not consume oxygen, thereby avoiding skewing the measurements at low oxygen levels.

Commercially available $pO_2$ sensors employ the dye tris(diphenylphenanthroline)ruthenium (II) chloride. Although this sensor has been proven in terms of accuracy and reliability for bioprocess monitoring, its sensitivity has to be significantly improved to meet the requirement for the $tcpO_2$ sensor 170A. To realize this goal, the original sensing dye is preferably replaced by fullerene C70, which is extremely sensitive to oxygen in the range of 0-0.228 Torr (26). Its maximum excitation wavelength is 470 nm, and its maximum emission is at 700 nm. The lifetime of this dye is approximately 20 ms in the absence of oxygen. The $tcpO_2$ sensor 170A will be prepared using the same proven technology as $pO_2$ sensors for bioprocess monitoring. The thickness of the $tcpO_2$ sensor 170A is preferably reduced relative to $pO_2$ sensors to shorten the response time to less than a few seconds.

The $tcpCO_2$ Sensor (170B)

Commercially available $pCO_2$ optical chemical sensors for bioprocess monitoring are based on the excitation-ratiometric fluorescent dye 8-hydroxypyrene-1,3,6-trisulfonic acid trisodium salt (HPTS) (27, 28). To construct these sensors, this dye is immobilized in a silicone rubber together with a phase transfer agent (a quaternary ammonium hydroxide, QAH) (27). QAH forms an ion pair with the indicator dye and helps to dissolve the dye into the hydrophobic polymer. It also helps trap some water that is required for production of carbonic acid and deprotonation of the dye.

Figure 6:
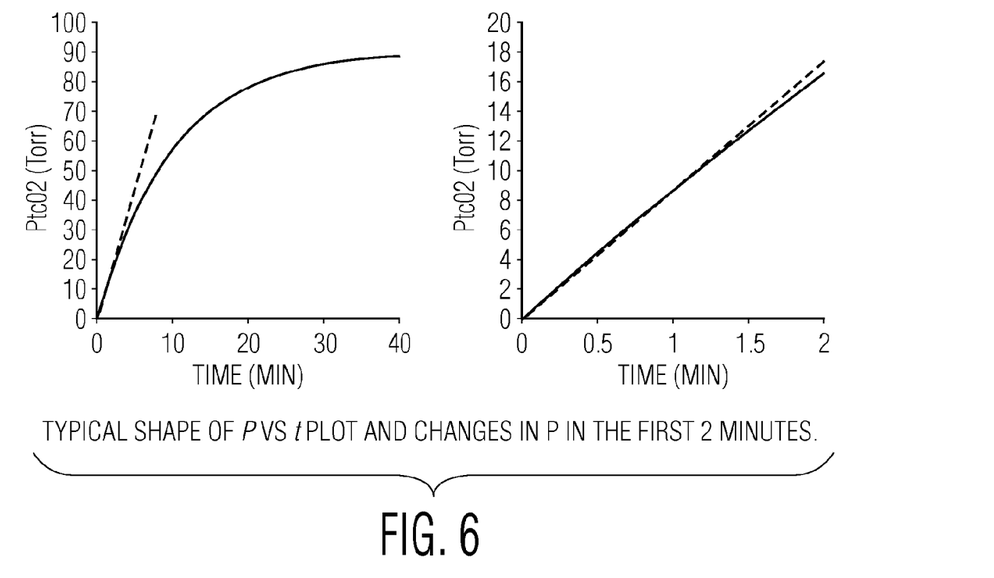
FIG. 6 are analytical time vs partial gas pressure plots for $ptcO_2$.

When $CO_2$ is present, it penetrates into this hydrophobic polymer forming carbonic acid with trapped water. The ratiometric pH indicator dissociates from the ion pair as it comes in contact with $H_2CO_3$ and becomes protonated. The protonated and deprotonated forms of the dye have distinct excitation maxima (405 and 455 nm), and the ratio of the two excitation peaks depends on the $CO_2$ concentration, as shown in FIG. 6. As in the lifetime measurements, this ratiometric approach is also known to eliminate the drawbacks of intensity-based measurements. Although this operational principle is similar to the Severinghaus electrode, these optical sensors have much better sensitivity.

These current $pCO_2$ optical chemical sensors have a responsive range between 0 and 20% $CO_2$ (0-152 Torr) with a limit of detection of 0.04% (0.3 Torr). As in the case of the $tcpO_2$ sensor 170A, the current $pCO_2$ sensors are preferably modified to significantly boost its sensitivity to ppm levels for use as the $tcpO_2$ sensor 170A. This can be done by reducing the QAH loading.

In a preliminary experiment, an off the shelf $pCO_2$ optical chemical sensor was tuned for use as the $tcpO_2$ sensor 170A and was able to detect changes in $pCO_2$ between 0 and 0.228 Torr (300 ppm) with a response of 9 minutes. For bioprocess monitoring, the 9-minute response time is fast enough as bioprocesses usually last from several hours to a few days. However, for $tcpCO_2$ measurements, it is desirable to shorten the sensor's response time to less than a few seconds. To significantly decrease the $tcpCO_2$ sensor 170A response time, the thickness of the $tcpCO_2$ sensor 170A is preferably reduced to a few microns. This will mean that the optical signal from the $tcpCO_2$ sensor 170A will be low and the optoelectronic components 130 need to be sensitive enough to measure the low signal.

Theory of Operation

Fickian diffusion of $O_2$ and $CO_2$ is observable out of a patient's foot into the nitrogen gas in the diffusion chamber 110. In this case, the mass balance equation for the diffusion chamber 110 and the measurement chamber 120 can be described as $$V\frac{dC}{dt} = kA(C_0 - C) \quad (1)$$

where V is the total volume of the two chambers, C is the concentration of oxygen or $CO_2$ in the chambers, t is time, k is the mass transfer coefficient, A is the total mass transfer area, and $C_0$ is the concentration of oxygen or $CO_2$ in the patient's arterial blood. Because C=P/RT, where P is the partial gas pressure, R is Boltzman constant, and T is the temperature, Equation (1) can be rewritten as $$V\frac{dP}{dt} = kA(P_0 - P) \quad (2)$$

At the beginning of each measurement (i.e. t=0), the partial pressures of oxygen and $CO_2$ in the chambers are equal to zero. Thus, the arterial blood gas partial pressure can be calculated by $$P_0 = B\frac{dP}{dt}\bigg|_{t=0} \quad (3)$$

where B=V/kA. B is a specific constant for each patient as a specific temperature.

The analytical solution to Equation (3) is plotted in FIG. 6. Note that the change in P with time is linear in the first 2 minutes of the measurements, and thus Equation (3) can be further simplified to $$P_0 = B\frac{\Delta P}{\Delta t} \quad (4)$$

Note that parameter B can be obtained by a single-point calibration versus the patient's arterial blood gas (ABG) value.

The rate expressed in Equation (4) should be proportional to the actual ABG $pO_2/pCO_2$. Also, by measuring the initial diffusion rate, one does not have to wait for equilibrium, which would take much longer than the few minutes each measurement cycle takes with the present invention. Although the circulating loop configuration of the embodiments of FIGS. 1A-3 will lead to greater gas dilution compared to direct skin contact measurements using conventional sensors, the extraordinary sensitivity of the optical chemical sensors to low concentrations (ppm levels) allow for this configuration to work.

The use of the two-chamber configuration (diffusion chamber 110 and measurement chamber 120) of FIGS. 1A-3 and the combined-chamber configuration of FIG. 4 also avoids direct exposure of the patient's skin to the high-intensity illumination of the optical chemical sensors 170A and 170B. Further, the lack of skin contact will eliminate motion artifacts. Problems such as diffusion variability due to differences in skin thickness, administration of vasopressors, etc. are avoided by performing measurements at two different temperatures.

The foregoing embodiments and advantages are merely exemplary, and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. Various changes may be made without departing from the spirit and scope of the invention, as defined in the following claims (after the Appendix below).

APPENDIX

1. Finer N, Leone T. Oxygen saturation monitoring for the preterm infant: the evidence basis for current practice. *Pediatr Res* 2009; 65 (4):375-80.
2. Saugstad O D. Is oxygen more toxic than currently believed? *Pediatrics* 2001; 108 (5):1203-5.
3. Cunningham S, Fleck B W, Elton R A et al. Transcutaneous oxygen levels in retinopathy of prematurity. *Lancet* 1995; 346 (8988):1464-5.
4. Carlo W A, Finer N N, Walsh M C et al. Target ranges of oxygen saturation in extremely preterm infants. *N Engl J Med* 2010; 362 (21):1959-69.
5. Chen M L, Guo L, Smith L E et al. High or low oxygen saturation and severe retinopathy of prematurity: a meta-analysis. Pediatrics 2010; 125 (6):1483-92.
6. Flynn J T, Bancalari E, Snyder E S et al. A cohort study of transcutaneous oxygen tension and the incidence and severity of retinopathy of prematurity. *N Engl J Med* 1992; 326 (16):1050-4.
7. Jobe A H. The new BPD: an arrest of lung development. *Pediatr Res* 1999; 46:641-3.
8. Jobe A H, Bancalari E. Bronchopulmonary dysplasia. *Am J Respir Crit Care Med* 2001; 163:1723-9.
9. Erickson S J, Grauaug A, Gurrin L et al. Hypocarbia in the ventilated preterm infant and its effect on intraventricular haemorrhage and bronchopulmonary dysplasia. *J Paediatr Child Health* 2002; 38 (6):560-2.
10. Gannon C M, Wiswell T E, Spitzer A R. Volutrauma, $PaCO_2$ levels, and neurodevelopmental sequelae following assisted ventilation. *Clin Perinatol* 1998; 25 (1):159-75.
11. Murase M, Ishida A. Early hypocarbia of preterm infants: its relationship to periventricular leukomalacia and cerebral palsy, and its perinatal risk factors. *Acta Paediatr* 2005; 94 (1):85-91.
12. Takahashi R, Yamada M, Takahashi T et al. Risk factors for cerebral palsy in preterm infants. *Early Hum Dev* 2005; 81 (6):545-53.
13. Garland J S, Buck R K, Allred E N et al. Hypocarbia before surfactant therapy appears to increase bronchopulmonary dysplasia risk in infants with respiratory distress syndrome. *Arch Pediatr Adolesc Med* 1995; 149 (6):617-22.
14. Hagen E W, Sadek-Badawi M, Carlton D P et al. Permissive hypercapnia and risk for brain injury and developmental impairment. *Pediatrics* 2008; 122 (3):583-9.
15. Kaiser J R, Gauss C H, Pont M M et al. Hypercapnia during the first 3 days of life is associated with severe intraventricular hemorrhage in very low birth weight infants. *J Perinatol* 2006; 26 (5):279-85.
16. Thome U H, Ambalavanan N. Permissive hypercapnia to decrease lung injury in ventilated preterm neonates. *Semin Fetal Neonatal Med* 2009; 14 (1):21-7.
17. Hauspurg A K, Allred E N, Vanderveen D K et al. Blood Gases and Retinopathy of Prematurity: The ELGAN Study. *Neonatology* 2010; 99 (2):104-11.
18. Severinghaus J W. The current status of transcutaneous blood gas analysis and monitoring. *Blood Gas News* 1998; 7 (2):4-9.
19. Quine D, Stenson B J. Does the monitoring method influence stability of oxygenation in preterm infants? A randomised crossover study of saturation versus transcutaneous monitoring. *Arch Dis Child Fetal Neonatal Ed* 2008; 93 (5):F347-50.
20. Tobias J D. Transcutaneous carbon dioxide monitoring in infants and children. *Pediatr Anesth* 2009; 19 (5):434-44.
21. Bernet-Buettiker V, Ugarte M J, Frey B et al. Evaluation of a new combined transcutaneous measurement of PCO2/pulse oximetry oxygen saturation ear sensor in newborn patients. *Pediatrics* 2005; 115 (1):e64-8.
22. Lacerenza S, De Carolis M P, Fusco F P et al. An evaluation of a new combined Spo2/PtcCO2 sensor in very low birth weight infants. *Anesth Analg* 2008; 107 (1):125-9.
23. Raju, T K, Stevenson, D K, Higgins, R D, Stark A R. Safe and Effective Devices for use in the Neonatal Intensive Care Units: NICHD Workshop Summary. Biomed *Instr Technol* 2009 43:408-418.
24. Szmacinski H, J. R. Lakowicz. Lifetime-Based Sensing. In: J R Lakowicz, editor, translator and editor *Topics In Fluorescence Spectroscopy*. New York: Plenum Press; 1994; p. 295.
25. Bambot S B, Holavanahali R, Lakowicz J R et al. Phase fluorometric sterilizable optical oxygen sensor. *Biotechnol Bioeng* 1994; 43 (11):1139-45.
26. Nagl S, Baleizao C, Borisov S M, Schaferling M. Optical Sensing and Imaging of Trace Oxygen with Record Response. Angew. *Chem. Int. Ed.* 2007, 46, 2317-2319.
27. Ge X D, Kostov Y, Rao G. High-stability non-invasive autoclavable naked optical $CO_2$ sensor. *Biosensors & Bioelectronics* 2003; 18 (7):857-65.
28. Ge X D, Kostov Y, Rao G. Low-cost noninvasive optical $CO_2$ sensing system for fermentation and cell culture. *Biotechnology and Bioengineering* 2005; 89 (3):329-34.
29. Tolosa L, Kostov Y, Harms P et al. Noninvasive measurement of dissolved oxygen in shake flasks. *Biotechnol Bioeng* 2002; 80 (5):594-7.

What is claimed is:

1. An analyte sensing system for determining a concentration of least one analyte present in an object ("analyte concentration") based on rates of diffusion prior to reaching equilibrium ("initial rates of diffusion"), comprising:
  a diffusion chamber adapted to receive at least a portion of an object containing at least one analyte to be measured;
  a measurement chamber pneumatically coupled to the diffusion chamber thereby adapted to receive at least a portion of one or more analytes from the diffusion chamber when the one or more analytes are present in the diffusion chamber;
  at least one sensor positioned in the measurement chamber that is adapted to chemically interact and/or to physically react with a respective analyte;
  at least one optoelectronic component positioned outside the measurement chamber for remotely detecting the chemical interaction and/or the physical reaction of the at least one sensor; and
  a controller for determining initial rates of diffusion of the at least one analyte being measured into the diffusion chamber based on signals received from the at least one optoelectronic component, wherein the controller determines the analyte concentration based on the determined initial rates of diffusion.

2. The system of claim 1, wherein the at least one sensor comprises at least one optical chemical sensor.

3. The system of claim 2, wherein the at least one optoelectronic component comprises:
    at least one optical excitation source for optically exciting the at least one optical chemical sensor; and
    at least one optical detector for detecting emission light from the at least one optical chemical sensor.

4. The system of claim 3, wherein the diffusion chamber is adapted to receive a human appendage.

5. The system of claim 4, wherein the at least one optical chemical sensor comprises a $pO_2$ optical chemical sensor and a $pCO_2$ optical chemical sensor.

6. The system of claim 5, wherein the controller controls the at least one optical excitation source and determines arterial blood gas concentration from signals received from the at least one optical detector.

7. The system of claim 5, wherein the pO2 optical chemical sensor comprises fullerene C70 and the pCO2 optical chemical sensor comprises 8-hydroxypyrene-1,3,6-trisulfonic acid trisodium salt (HPTS).

8. A non-invasive transcutaneous blood gas sensing system for determining a concentration of at least one arterial blood gas ("arterial blood gas concentration") in a mammal based on rates of diffusion prior to reaching equilibrium ("initial rates of diffusion"), comprising:
    a diffusion chamber adapted to receive a mammalian appendage;
    a measurement chamber pneumatically coupled to the diffusion chamber, thereby adapted to receive at least a portion of one or more arterial blood gases from the diffusion chamber when the one or more arterial blood gases diffuse transcutaneously from the mammalian appendage into the diffusion chamber;
    at least one optical chemical sensor positioned in the measurement chamber that is adapted to chemically interact and/or physically react with a respective arterial blood gas;
    at least one optoelectronic component positioned outside the measurement chamber for remotely detecting the chemical interaction and/or the physical interaction of the at least one optical chemical sensor; and
    a controller for determining initial rates of diffusion of the at least one arterial blood gas being measured into the diffusion chamber based on signals received from the at least one optoelectronic component, wherein the controller determines the arterial blood gas concentration based on the determined initial rates of diffusion.

9. The system of claim 8, wherein the diffusion chamber and the measurement chamber are pneumatically coupled to at least one pneumatic pump.

10. The system of claim 9, wherein the diffusion chamber, the measurement chamber and the pneumatic pump are pneumatically coupled with conduits and together form a circulation loop.

11. The system of claim 10, further comprising a first valve pneumatically coupled to the circulation loop for selectively introducing ambient air or nitrogen into the circulation loop.

12. The system of claim 11, further comprising a second valve pneumatically coupled to the circulation loop for selectively exhausting air and/or nitrogen from the circulation loop.

13. The system of claim 8, wherein the at least one optoelectronic component comprises:
    at least one optical excitation source for optically exciting the at least one optical chemical sensor; and
    at least one optical detector for detecting emission light from the at least one optical chemical sensor.

14. The system of claim 8, wherein the at least one optical chemical sensor comprises a $pO_2$ optical chemical sensor and a $pCO_2$ optical chemical sensor.

15. The system of claim 14, wherein the controller controls the at least one optical excitation source and determines arterial blood gas concentration from signals received from the at least one optical detector.

16. The system of claim 14, wherein the $pO_2$ optical chemical sensor comprises fullerene C70 and the $pCO_2$ optical chemical sensor comprises 8-hydroxypyrene-1,3,6-trisulfonic acid trisodium salt (HPTS).

17. The system of claim 15, wherein the controller determines a change in $O_2$ partial pressure and a change in $CO_2$ partial pressure in the measurement chamber as a function of time based on the signals received from the at least one optical detector.

18. The system of claim 17, wherein the controller determines mammalian arterial blood gas concentration based on the changes in $O_2$ and $CO_2$ partial pressures in the measurement chamber prior to the $O_2$ and $CO_2$ partial pressures reaching an equilibrium state.

19. The system of claim 18, wherein the controller determines mammalian arterial blood gas concentration based on substantially linear changes in $O_2$ and $CO_2$ partial pressures in the measurement chamber as a function of time.

20. The system of claim 8, wherein the diffusion chamber is shaped to receive and fit a human foot.

21. A non-invasive transcutaneous blood gas sensing system for determining a concentration of at least one arterial blood gas ("arterial blood gas concetration") in a mammal based on rates of diffusion prior to reaching equilibrium ("initial rates of diffusion"), comprising:
    a combined diffusion and measurement chamber comprising at least one gas permeable surface adapted to allow transcutaneous diffusion of one or more arterial blood gases from a mammal when the gas permeable surface is in contact with the mammal;
    at least one optical chemical sensor positioned in the combined diffusion and measurement chamber that is adapted to chemically interact and/or physically react with a respective arterial blood gas; and
    an optoelectronic system positioned outside the combined diffusion and measurement chamber for remotely detecting the chemical interaction and/or the physical interaction of the at least one optical chemical sensor; and
    a controller for determining initial rates of diffusion of the at least one arterial blood gas being measured into the combined diffusion and measurement chamber based on signals received from the at least one optoelectronic system, wherein the controller determines the arterial blood gas concentration based on the determined initial rates of diffusion.

22. The system of claim 21, further comprising an inlet port coupled to the combined diffusion and measurement chamber for selectively introducing air and/or nitrogen into the combined diffusion and measurement chamber.

23. The system of claim 22, further comprising an exhaust port coupled to the combined diffusion and measurement chamber for selectively exhausting air and/or nitrogen from the combined diffusion and measurement chamber.

24. The system of claim 21, wherein the optoelectronic system comprises:
- at least one optical excitation source for optically exciting the at least one optical chemical sensor; and
- at least one optical detector for detecting emission light from the at least one optical chemical sensor.

25. The system of claim 21, wherein the at least one optical chemical sensor comprises a $pO_2$ optical chemical sensor and a $pCO_2$ optical chemical sensor.

26. The system of claim 24, wherein the controller controls the at least one optical excitation source and determines arterial blood gas concentration from signals received from the at least one optical detector.

27. The system of claim 25, wherein the $pO_2$ optical chemical sensor comprises fullerene C70 and the $pCO_2$ optical chemical sensor comprises 8-hydroxypyrene-1,3,6-trisulfonic acid trisodium salt (HPTS).

28. The system of claim 26, wherein the controller determines the change in $pO_2$ partial pressure and the change in $pCO_2$ partial pressure in the combined diffusion and measurement chamber as a function of time based on the signals received from the at least one optical detector.

29. The system of claim 28, wherein the controller determines mammalian arterial blood gas concentration based on the changes in $O_2$ and $CO_2$ partial pressures in the measurement chamber prior to the $O_2$ and $CO_2$ partial pressures reaching an equilibrium state.

30. The system of claim 29, wherein the controller determines mammalian arterial blood gas concentration information based on substantially linear changes in $O_2$ and $CO_2$ partial pressures in the measurement chamber as a function of time.

31. A method of measuring at least one analyte that is contained in an object that is at least partially permeable to the at least one analyte, comprising the steps of:
- inserting at least a portion of the object that contains the at least one analyte into a diffusion chamber that is pneumatically coupled to a measurement chamber that contains at least one analyte sensor, wherein the pneumatically coupled diffusion and measurement chambers form a circulation loop;
- opening the circulation loop to flush the diffusion chamber with nitrogen until the at least one analyte sensor outputs a predetermined baseline reading;
- closing the circulation loop and circulating nitrogen continuously around the circulation loop;
- determining a change in the at least one analyte partial pressure in the measurement chamber as a function of time; and
- determining a concentration of the at least one analyte in the object based on changes in the at least one analyte partial pressure in the measurement chamber prior to the at least one analyte partial pressure in the measurement chamber reaching an equilibrium state.

32. The method of claim 31, wherein the object comprises a mammalian appendage.

33. The method of claim 32, wherein the object comprises a human appendage and the at least one analyte comprises $O_2$ and $CO_2$.

34. A method of measuring at least one analyte that is contained in an object that is at least partially permeable to the at least one analyte, comprising the steps of:
- providing a combined diffusion and measurement chamber that contains at least one analyte sensor and that comprises a diffusion surface that is at least partially permeable to the at least one analyte;
- flushing the combined diffusion and measurement chamber with nitrogen until the at least one analyte sensor outputs a predetermined baseline reading;
- isolating the combined diffusion and measurement chamber from its surrounding atmosphere;
- placing the diffusion surface in physical contact with a surface of the object;
- determining a change in the at least one analyte partial pressure in the combined diffusion and measurement chamber as a function of time; and
- determining a concentration of the at least one analyte in the object based on changes in the at least one analyte partial pressure in the measurement chamber prior to the at least one analyte partial pressure in the measurement chamber reaching an equilibrium state.

35. The method of claim 31, wherein the object comprises a mammalian appendage.

36. The method of claim 32, wherein the object comprises a human appendage and the at least one analyte comprises $O_2$ and $CO_2$.

* * * * *